United States Patent [19]
Louis et al.

[11] Patent Number: 6,136,000
[45] Date of Patent: Oct. 24, 2000

[54] ANCHORING DEVICE FOR POSTERIOR VERTEBRAL OSTEOSYNTHESIS

[76] Inventors: René Louis, 4bis impasse du Roc Fleuri, 13008 Marseille; Christian Louis, 17 chemin Colline Saint-Joseph, 13009 Marseille, both of France

[21] Appl. No.: 08/930,393
[22] PCT Filed: Jan. 17, 1997
[86] PCT No.: PCT/FR97/00088
  § 371 Date: Sep. 18, 1997
  § 102(e) Date: Sep. 18, 1997
[87] PCT Pub. No.: WO97/25931
  PCT Pub. Date: Jul. 24, 1997

[51] Int. Cl.[7] .................................................. A61B 17/56
[52] U.S. Cl. ............................................. 606/61; 600/60
[58] Field of Search .................................. 606/61, 62, 63, 606/64, 65, 54; 128/69, 68, 75, 78

[56] References Cited

U.S. PATENT DOCUMENTS

| | | | |
|---|---|---|---|
| 4,257,409 | 3/1981 | Bacal et al. | 128/69 |
| 5,116,334 | 5/1992 | Cozad et al. | 606/61 |

*Primary Examiner*—Michael Buiz
*Assistant Examiner*—Vy Q. Bui
*Attorney, Agent, or Firm*—Blakely Sokoloff Taylor & Zafman

[57] ABSTRACT

Osteosynthesis implants for use in the backbone of the human or animal skeleton are disclosed. The anchoring device for posterior vertebral osteosynthesis comprises at least four fixation points each consisting of a hook (4, 5, 6, 7). The hooks are arranged in opposed pairs along perpendicular axes XX' and ZZ', and each pair of hooks forms a gripping assembly, of which one is a lateral or isthmian assembly along axis XX' while the other is an axial or laminar assembly along axis ZZ'.

18 Claims, 3 Drawing Sheets

ANCHORING DEVICE FOR POSTERIOR VERTEBRAL OSTEOSYNTHESIS

This invention relates to an anchoring device for posterior vertebral osteosynthesis.

The technical field of the invention is the domain of the manufacture of osteosynthesis implants intended for the vertebral column of man or of an animal.

When it is desirable to stabilize or to fix two or several vertebrae to one another and/or to reduce deformations of the vertebral column (such as cyphosis or scoliosis), it is known to use longitudinal metal devices that bridge several vertebrae, for example with plates or rods, and onto which are anchored other metal fixing elements such as screws.

Various patent applications have been made, in particular for different vertebral osteosynthesis systems, such as, for example application No. FR 2 716 794, published Sep. 8th, 1995 and applied for by the American company SOFAMOR (Inventor: Mr. STEIB) for a "Connector for the implementation of rachidian osteosynthesis intended for lumbar or sacral or iliosacral fixing" or the application No. FR 2 712 486 published May 24th, 1995 by Messrs. BRESLAV, CATON etc . . . for an "Intervertebral prosthesis" or the application No. FR 2 697 874, published May 13th, 1994 by the Société de Fabrication de Matériel Orthopédique (Inventor: Mr. COTREL) entitled "A connecting device for a long thin element and for a support for this element".

Other older applications can also be mentioned, such as the application No. FR 2 672 202 published Aug. 7th, 1992, by the company SAFIR (Inventors Mr GRAF et al.) for a "Surgical bone implant, notably for an intervertebral stabilizer" or the application No. FR 2 651 992, published Mar. 22nd, 1991 by the Société de Fabrication de Matériel Orthopédique (Inventor: Mr. LAURAIN) for "An implant for anterior dorso-lumbar rachidian osteosynthesis, intended for the correction of cyphosis".

All these systems, like many others, too numerous to mention here, essentially use for their fixing onto the vertebrae, screws that require tapping into the bony parts, which is rather delicate and is in any case at the expense of bone fragility. There are also systems based on hooks or on strapping around the blade, spinal, transverse or articular (but never isthmic) regions of each vertebra, but these regions, considered to be rather fragile, do not alone allow large correction torques to be applied.

Hence the problem posed is to be able to produce vertebral osteosynthesis systems while using anchoring devices which are not screwed into the vertebrae but are fixed sufficiently rigidly to them to allow large correction torques to be applied without weakening or risking damage to said vertebrae.

A solution to the problem posed is an anchoring device for posterior vertebral osteosynthesis that comprises at least four fixing points, each constituted by a hook, the hooks being opposed to one another, two by two, along two perpendicular axes XX'/ZZ' and each pair of hooks thereby set up, forming a clamp, the one considered to be along the lateral axis XX' referred to as isthmic and the other axial one ZZ' referred to as laminar; said hooks are rigidly attached to supports that connect them to one and the same central body, preferably a single solid block and the ends of these hooks are of a width of at least 5 millimeters.

The central body receives a fixing means immobilising on itself any means of connecting with at least one other anchoring device, such as at least one rod; the fixing means for this can then be a collar that straddles it and immobilizes it on said central body by clamping.

In one preferred embodiment, each support of each of said hooks or each pair defined above is slidably mounted with respect to said central body and is adjustable along the axes ZZ'/XX' which allows them to be brought closer together or moved further apart, said hook supports sliding within said central body being able to be immobilized within it by any means going through said central body, such as, for example locking screws.

Such a system deals very well with the problem posed by, in effect allowing an anchorage on each posterior arc of the vertebra, as shown in FIGS. 4 and 5; the two hooks referred to as isthmic, as defined above, laterally opposed along the horizontal axis XX' of the device once in position, when the person concerned is in the standing position, can hook onto the right and left isthmic regions of the vertebra at the posterior part of the foramina, which are the conjugation holes through which the rachidian nerves emerge, something which has never been done up to the present time; the two other hooks which are axially opposed and arranged along a perpendicular axis ZZ', hence vertical once in position, hook onto the middle of the upper and lower edges of the blades of the same vertebra; these hook assemblies thereby form two perpendicular grips, rigidly fixed by a common component that crosses over their supports.

In one particular embodiment, the supports of the hooks referred to as isthmic, arranged laterally on the isthmic regions, are constituted by two cylindrical concentric shafts sliding one inside the other, of circular cross section and which permit the rotation of said hooks about their locking axis thereby providing perfect adaptation of the anchorage to the morphology of the vertebra.

The supports of the hooks referred to as laminar, arranged axially or vertically in order to hook onto the upper and lower edges of the blades of the same vertebra, can be constituted preferably by two cylindrical but non-circular guides that slide and fit one inside the other, and which co-operate with a rail from the central body that then prevents their rotation with respect to their locking axis so as to immobilize said central body on the vertebra.

The sliding supports of each hook makes it possible to match the length of the collar that they form to the size of the vertebra onto which it is desirable to anchor, without requiring any operation on the bone of the vertebra and hence avoiding any weakening of it, whilst providing, by means of the tetrapod thereby constituted, a perfect anchorage that allows large traction and torsion forces.

The hooks existing at the present time, such as those mentioned previously, are always narrow, possibly pointed or rounded off at their end and are never supported on the vertical isthmuses, nor combined with other hooks arranged on the median line of the upper and lower vertebral blades.

The result is a new device for posterior vertebral osteosynthesis anchorage, that constitutes this invention, advantages of which other than those mentioned above could be mentioned but sufficient of which have already been pointed out to prove the novelty and the interest of it.

The description and the Figures below represent one example of an embodiment of the invention which has no limitative character whatsoever: other embodiments are possible, within the context of the scope and the extent of this invention, in particular by changing the shape of the various hook supports and of the central body supporting said supports and the connecting means between successive anchorage devices.

Figure 1:
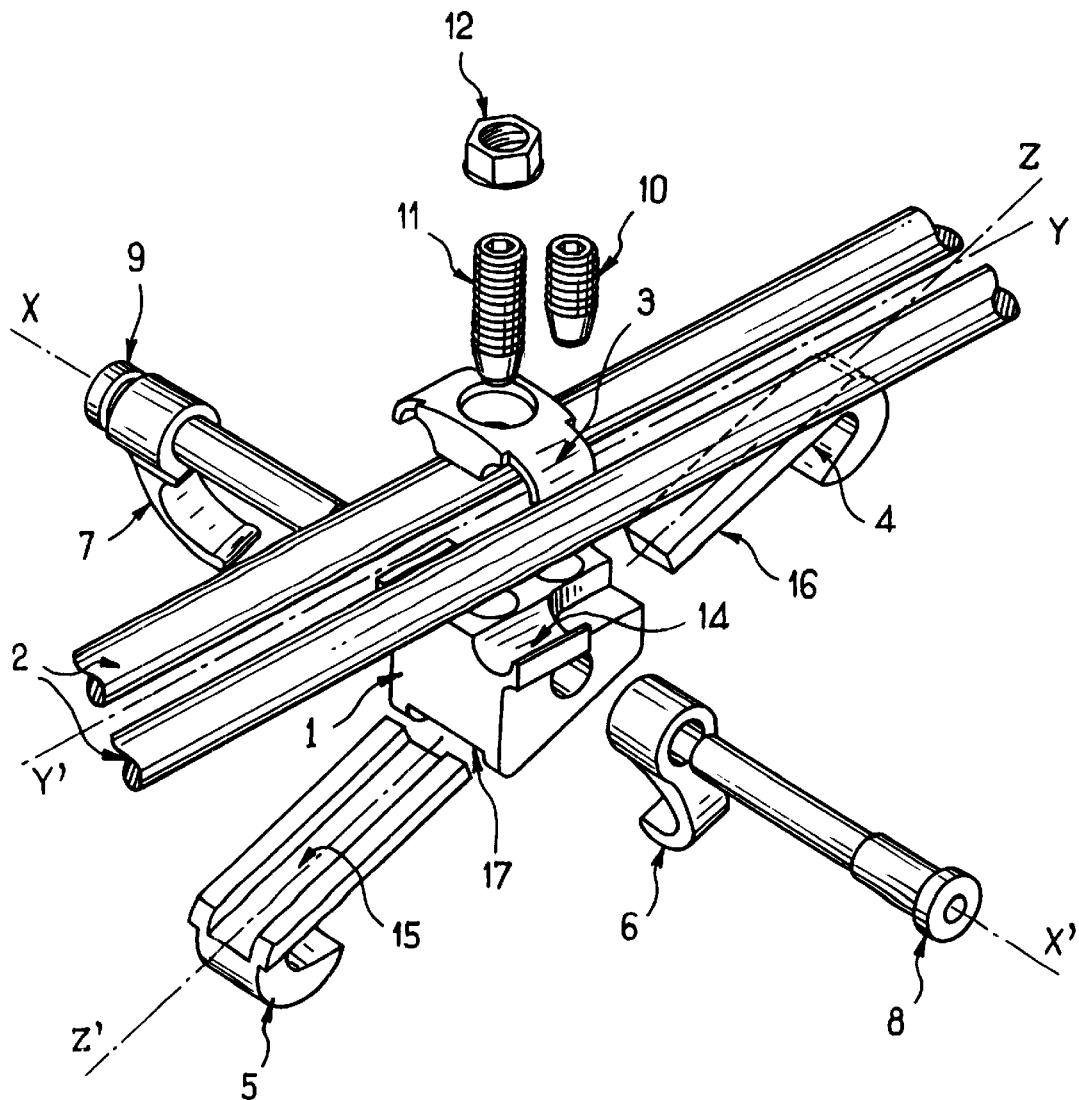
FIG. 1 represents a device according to the invention, in an exploded perspective view, each element being disassembled.

The anchoring device for posterior vertebral osteosynthesis on a vertebra 13, comprises according to the invention at least four fixing points, each constituted by a hook 4, 5, 6, 7, the hooks being opposed to one another, two by two, along two perpendicular axes, XX' horizontal once put into position given that the person concerned is in the standing position, and ZZ' vertical with each pair thereby constituted, forming a clamp.

The ends of said hooks 4, 5, 6, 7 are sufficiently wide to provide a spreading of the support and the clamping force on the parts of the vertebra, whilst preventing any rotation of the device, thereby limiting its possible displacement with respect to said vertebra on which it is anchored.

For this, the width of the ends of said hooks may be, for example, at least 5 millimeters at the surface where they press on the parts of the vertebra receiving said hooks.

As previously indicated, they are rigidly fixed to supports that connect them to one and the same central body 1, preferably a single solid block, the supports slide and are adjustable with respect to the block along axes respectively ZZ' for the vertical pair 4, 5 and XX' for the horizontal pair 6, 7 allowing said hooks to move closer together or move further apart from one another.

Regarding the lateral hooks 6, 7 referred to as isthmic hooks, their supports can be two cylindrical and concentric shafts 8, 9, one of which can be hollowed out to allow the other male shaft 8 to be introduced, one of them then sliding within and with respect to the other, until blocked by their respective ends which are formed into heads, said lateral hooks 6, 7 on the outside of the isthmic regions 19 at the posterior part of the foramina 18 of the vertebra 13; the circular cross section of said shafts allowing their rotation and/or that of the hooks 6, 7 in order to match any angular orientation of the isthmic regions with respect to the axis ZZ' of the device and/or YY' of the line of the vertebral column to be corrected.

Contrary to this, the sliding supports 15, 16 of the hooks, one called supra-laminar 5 on the upper part and the other called infra-laminar 4 on the lower part, arranged along the vertical axis ZZ' corresponding to the blades 20 of the same vertebra 13, are constituted by at least two guides that are cylindrical but noncircular that slide and fit one inside the other, cooperating with a rail 17 from the central body 1, preventing rotation of said supports with respect to the axis ZZ', as shown in the attached Figures: the support 15 of hook 5 has, for example a U-shaped cross section, on the inside of which the support 16 of hook 4 of rectangular section can slide, the whole being held in a guide 17 of internal section corresponding to the external shape, also rectangular of the support 15, in the central single block body 1.

The assembly of said supports, four in number, according to this embodiment represented in the Figures slides within said central body 1 where they are immobilized by any means passing through it, such as, for example, locking screws 10, 11 screwed into the central body with their ends supported on said respective supports that they are being used to lock.

Figure 2:
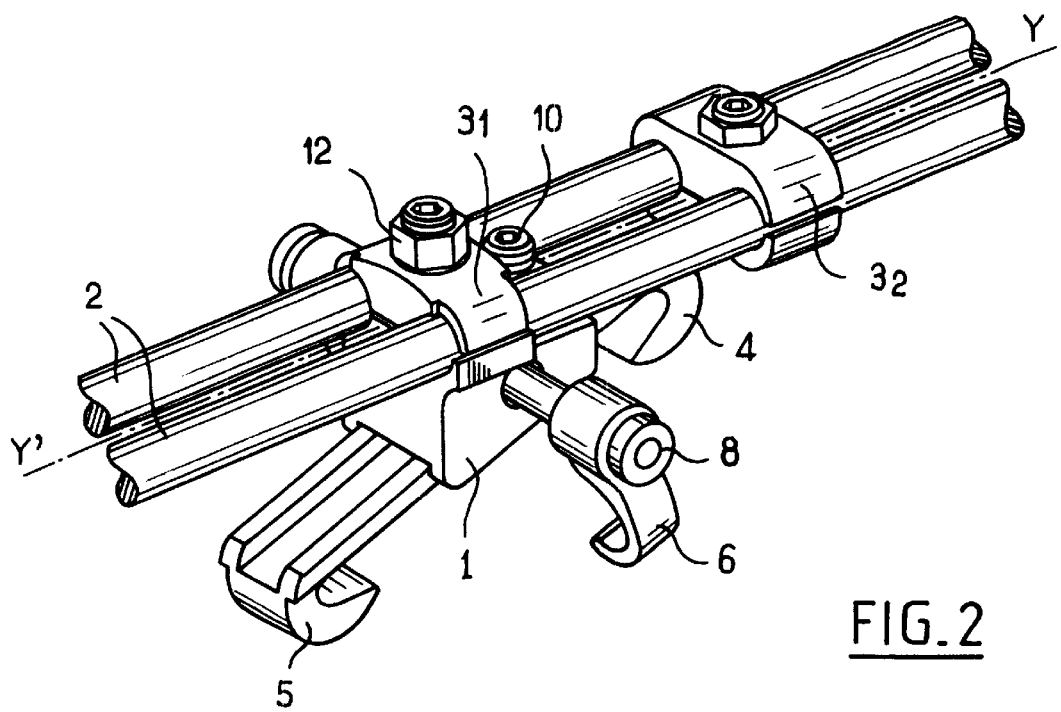
FIG. 2 is a perspective view of the same device as FIG. 1 but assembled.
Figure 3:
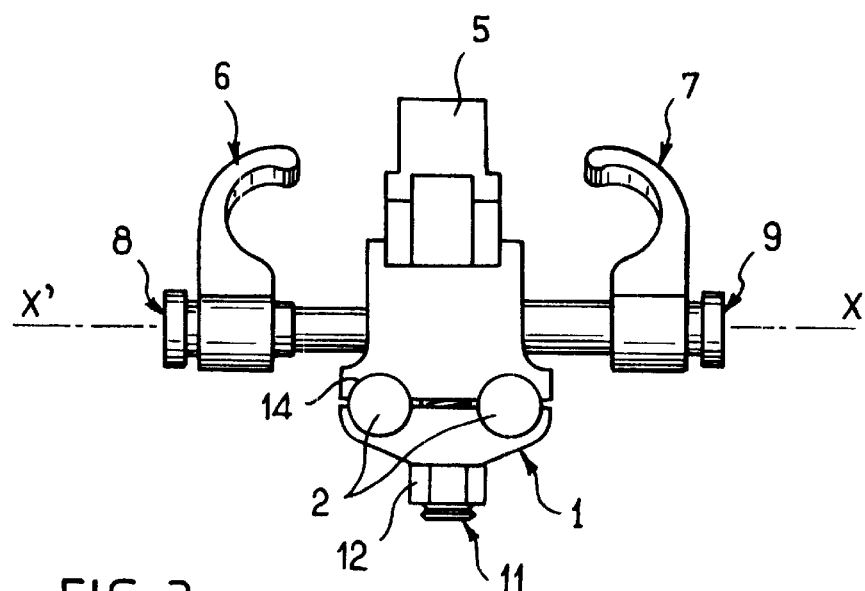
FIG. 3 is a view of one of the devices of the preceding Figures in a cranial view, therefore from above once put into position.

The common component or single block central body 1 includes, close to its upper median line with respect to the hooks, at least one gutter 14 in which any connecting means, such as a longitudinal metal rod can be housed and locked, with another anchoring device 32 as shown in FIG. 2 by its single means of fixing said device onto said rods 2.

Preferably, said connecting means is constituted by two metal rods 2 and the means of fixing them onto said central body into the two gutters 14, is a collar 3 that straddles said rods and immobilizes them on the central body 1 by clamping, the clamping being carried out by a nut 12 screwed onto one of said means of immobilising the hook supports such as one of the locking screws 10, 11.

The two longitudinal metal rods 2 are of a length suited to the length of the vertebral column that can be treated in accordance with the desired assembly.

An ancillary system of instruments then makes it possible to separate or bring closer together the tetrapods or double clamps thereby constituted and fixed onto two or more vertebrae in order to extend or curtail a vertebral curvature, their fixing by clamping at four points allowing such a force without risk.

Temporary rods can be fixed onto the isthmic rods that allow a de-rotation effect to be exerted on the vertebrae 13 and the two posterior, axial paramedian rods 2, precurved in accordance with the desired final shape of the spine, are used to block the tetrapods through their fixing and immobilization clamp 3, after a reduction of the deformation.

The assembly can be accompanied by bone grafts without any obligation to later remove said system, but such a disassembly is in any case easy to carry out by unscrewing the various locking systems 12, 10, 11 and dismantling from the assembly components that slide with respect to one another and are therefore easy to take out.

Figure 4:
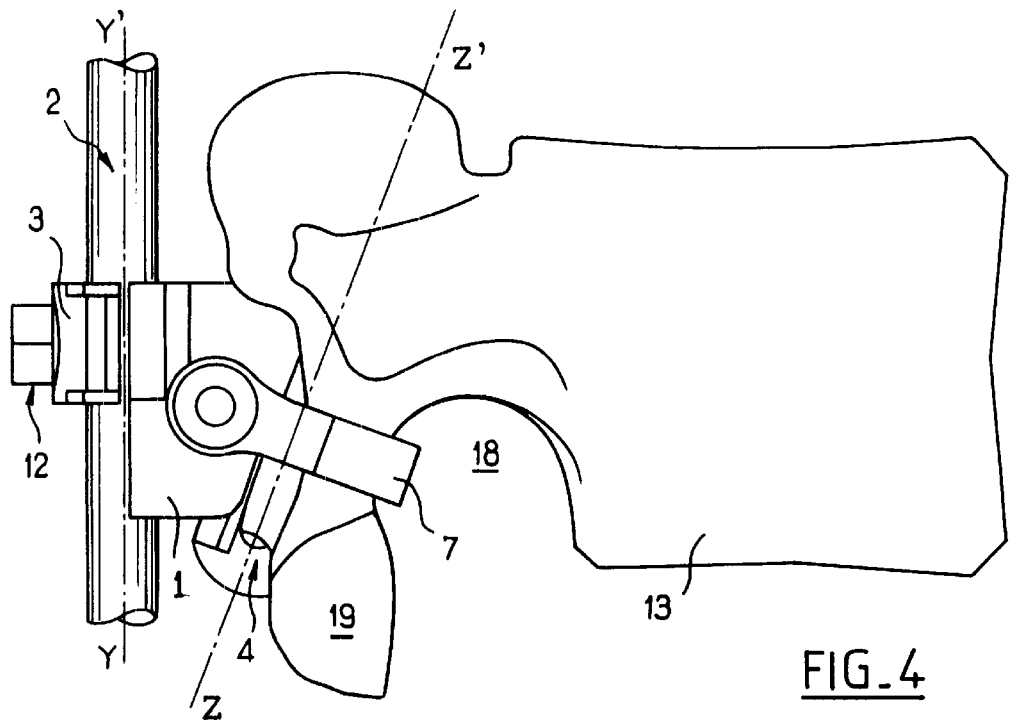
FIG. 4 is a straight lateral view of the same device anchored onto a vertebra.
Figure 5:
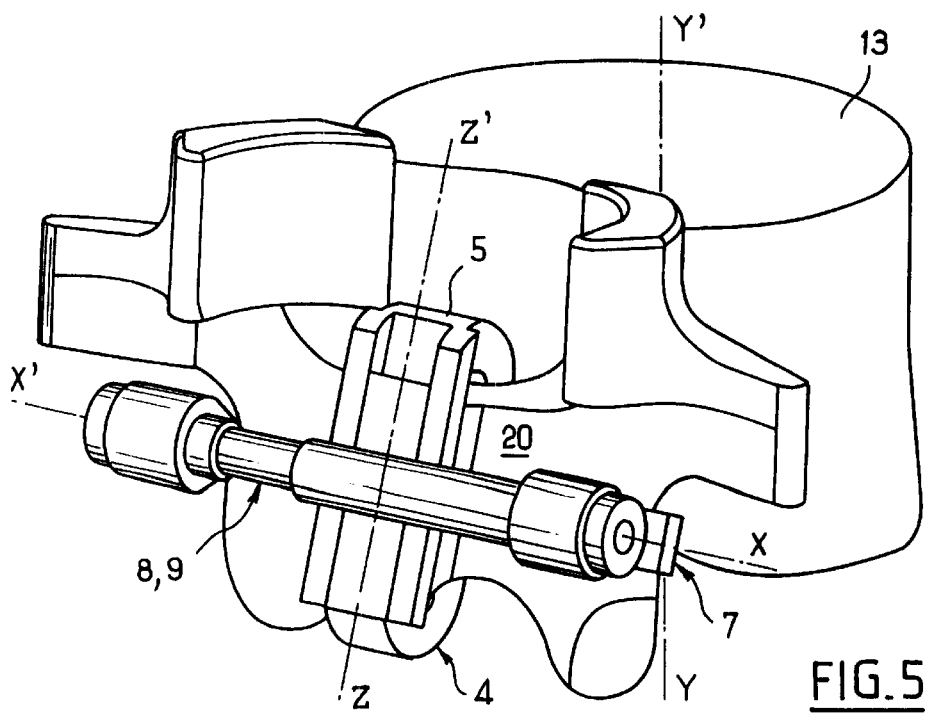
FIG. 5 is a simplified diagrammatic view of the individual hooks and their support put into position, in accordance with FIG. 4.

It should be remarked that, in FIGS. 4 and 5, due to the morphology of the vertebrae, the axes ZZ' of the hooks called vertical or laminar 4, 5 and YY' of the connecting means 2, corresponding in fact to that of the axis of the vertebra 13, form an angle open towards the top, ZZ' moving away from YY' in the direction of the hands of a watch; while in FIGS. 1 and 2, the device is represented in fact upside down, the part normally at the top being directed towards the bottom.

What is claimed is:

1. An anchoring device for attaching to at least a first vertebra (13), the device having two perpendicular axes ZZ'/XX' and comprising:

a first vertebral hook (4) defining a first fixing point;

a second vertebral hook (5) defining a second fixing point, the second vertebral hook (5) opposed to the first vertebral hook (4) along the ZZ' axis to form a pair of laminar hooks;

a third vertebral hook (6) defining a third fixing point;

a fourth vertebral hook (7) defining a fourth fixing point, the fourth vertebral hook (7) opposed to the third vertebral hook (6) along the XX' axis to form a pair of isthmic hooks;

a central body (1);

a laminar support that rigidly attaches the laminar hooks to the central body (1) along the ZZ' axis; and an isthmic support that rigidly attaches the isthmic hooks to the central body along the XX' axis, wherein the laminar hooks and the isthmic hooks form a clamp that is adapted to fix the device to one vertebra (13) by distributing the fixing forces over at least the four fixing points while maintaining axes ZZ'/XX' substantially perpendicular.

2. The anchoring device of claim 1 further comprising:
means for connecting the central body (1) of the anchoring device fixed to the first vertebra (13) to the central body (1) of a second anchoring device fixed to a second vertebra; and
means for fixing (3) the means for connecting to the central body (1) of the anchoring device.

3. The anchoring device of claim 1 wherein each of the laminar support and the isthmic support is slidably mounted along its axis, ZZ' and XX' respectively, and with respect to the central body (1).

4. The anchoring device of claim 3 further comprising:
means for immobilizing the laminar support with respect to the central body (1) and the isthmic support with respect to the central body (1).

5. The anchoring device of claim 4 wherein the means for immobilizing the laminar support with respect to the central body (1) is a first locking screw (10) and for immobilizing the isthmic support with respect to the central body (1) is a second locking screw (11), wherein the central body (1) is adapted to receive the first locking screw (10) and the second locking screw (11) there through.

6. The anchoring device of claim 2 wherein the means for connecting is at least one rod (2) and the means for fixing is a collar (3) that straddles the at least one rod (2).

7. The anchoring device of claim 6, the collar (3) having a locking screw (11) disposed through the collar (3) and into the central body (1) and having a nut (12) screwed onto the locking screw (11) to clamp the at least one rod (2) to the central body (1).

8. The anchoring device of claim 7, support having two cylindrical concentric shafts, male shaft (8) and female shaft (9), that are adapted to slide about one another and to permit the rotation of the third and fourth vertebral hooks (6, 7) with respect to the central body (1) about the axis XX'.

9. The anchoring device of claim 8, the central body (1) having a rail (17) formed therein and the laminar support having two cylindrical guides, female sliding support (15) and male sliding support (16), that are adapted to slide about one another and, in cooperation with the rail (17), are adapted to prevent the rotation of female sliding support (15) and male sliding support (16) with respect to the central body (1) about the axis ZZ'.

10. The anchoring device of claim 9, the first vertebra (13) having right and left foramina (18), the right and left foramina (18) having a posterior part, wherein the third vertebral hook (6) and the fourth vertebral hook (7) are adapted to hook onto the posterior part of the right and left foramina (18) of the first vertebra (13).

11. The anchoring device of claim 10, the first vertebra (13) having an upper and lower blades (20), each of the upper and lower blades (20) having an edge having a middle, wherein the first vertebral hook (4) and the second vertebral hook (5) are adapted to hook onto the middle of the upper and lower edges of the blades (20) of the first vertebra (13).

12. The anchoring device of claim 5, the isthmic support having two cylindrical concentric shafts, male shaft (8) and female shaft (9), that are adapted to slide about one another and to permit the rotation of the third and fourth vertebral hooks (6, 7) with respect to the central body (1) about the axis XX'.

13. The anchoring device of claim 12, the central body (1) having a rail (17) formed therein and the laminar support having two cylindrical guides, female sliding support (15) and male sliding support (16), that are adapted to slide about one another and, in cooperation with the rail (17), are adapted to prevent the rotation of female sliding support (15) and male sliding support (16) with respect to the central body (1) about the axis ZZ'.

14. The anchoring device of claim 13, the first vertebra (13) having right and left foramina (18), the right and left foramina (18) having a posterior part, wherein the third vertebral hook (6) and the fourth vertebral hook (7) are adapted to hook onto the posterior part of the right and left foramina (18) of the first vertebra (13).

15. The anchoring device of claim 14, the first vertebra (13) having an upper and lower blades (20), each of the upper and lower blades (20) having an edge having a middle, wherein the first vertebral hook (4) and the second vertebral hook (5) are adapted to hook onto the the middle of the upper and lower edges of the blades (20) of the first vertebra (13).

16. A method of fixing an anchoring device to at least a first vertebra (13), the device having two perpendicular axes ZZ'/XX', a first vertebral hook (4) defining a first fixing point, a second vertebral hook (5) defining a second fixing point, the second vertebral hook (5) opposed to the first vertebral hook (4) along the ZZ' axis to form a pair of laminar hooks, a third vertebral hook (6) defining a third fixing point, and a fourth vertebral hook (7) defining a fourth fixing point, the fourth vertebral hook (7) opposed to the third vertebral hook (6) along the XX' axis to form a pair of isthmic hooks, a central body (1) coupled to the pair of laminar hooks and coupled to the pair of isthmic hooks, the method comprising:
clamping the laminar hooks and the isthmic hooks to the first vertebra (13) by distributing the fixing forces over at least the four fixing points while maintaining axes ZZ'/XX' substantially perpendicular.

17. The method of claim 16, the first vertebra (13) having a right and left foramina (18), the right and left foramina (18) having a posterior part, wherein the step of clamping the isthmic hooks to the first vertebra (13) comprises:
hooking the third vertebral hook (6) to the left foramen (18) of the first vertebra (13); and
hooking the fourth vertebral hook (7) to the right foramen (18) of the first vertebra (13).

18. The method of claim 17, the first vertebra (13) having an upper and lower blades (20), each of the upper and lower blades (20) having an edge having a middle, wherein the step of clamping the laminar hooks to the first vertebra (13) comprises the steps of:
hooking the first vertebral hook (4) to the middle of the lower edge of the blades (20) of the first vertebra (13); and
hooking the second vertebral hook (5) to the upper edge of the blades (20) of the first vertebra (13).

\* \* \* \* \*